US010172579B2

(12) United States Patent
Yang (10) Patent No.: US 10,172,579 B2
(45) Date of Patent: Jan. 8, 2019

(54) X-RAY IMAGING SYSTEM

(71) Applicant: SAMSUNG ELECTRONICS CO., LTD., Suwon-si (KR)

(72) Inventor: Chang Jin Yang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 241 days.

(21) Appl. No.: 14/906,427

(22) PCT Filed: Jul. 25, 2014

(86) PCT No.: PCT/KR2014/006824
§ 371 (c)(1),
(2) Date: Jan. 20, 2016

(87) PCT Pub. No.: WO2015/012643
PCT Pub. Date: Jan. 29, 2015

(65) Prior Publication Data
US 2016/0151030 A1 Jun. 2, 2016

(30) Foreign Application Priority Data
Jul. 26, 2013 (KR) .................... 10-2013-0088622

(51) Int. Cl.
*A61B 6/00* (2006.01)
*A61B 6/04* (2006.01)

(52) U.S. Cl.
CPC .......... *A61B 6/4429* (2013.01); *A61B 6/0407* (2013.01); *A61B 6/42* (2013.01)

(58) Field of Classification Search
CPC ........ A61B 6/42; A61B 6/0407; A61B 6/4429
See application file for complete search history.

(56) References Cited

U.S. PATENT DOCUMENTS

| 4,948,208 A * | 8/1990 | Schubert ................. F16C 29/00 248/206.5 |
| 2005/0152503 A1* | 7/2005 | Rauh ........................ A61B 6/00 378/209 |

FOREIGN PATENT DOCUMENTS

| CN | 2648769 Y | 10/2004 |
| JP | 03147195 A * | 6/1991 |

(Continued)

OTHER PUBLICATIONS

International Search Report, issued by International Searching Authority in corresponding International Application No. PCT/KR2014/006824, dated Oct. 28, 2014, (PCT/ISA/210).

(Continued)

*Primary Examiner* — Chih-Cheng Kao
(74) *Attorney, Agent, or Firm* — Sughrue Mion, PLLC (57) ABSTRACT

An x-ray imaging system is provided. The x-ray imaging system includes an imaging apparatus configured to generate x-rays and image a subject by radiating the x-rays, an x-ray detection apparatus configured to detect the x-rays by receiving the x-rays radiated by the imaging apparatus, a table on which the subject is positioned, an accommodation frame provided on at least one portion of the table wherein the x-ray detection apparatus is accommodated in the accommodation frame, and a rail unit coupled to an inner side of the accommodation frame configured to at least one of withdraw the x-ray detection apparatus into the accommodation frame and accommodate the x-ray detection apparatus in the accommodation frame, wherein the rail unit comprises a first rail member positioned at an outer side, a second rail member positioned at an inner side of the first rail member, a third rail member positioned in between the first rail member and the second rail member, and a coupling (Continued)

member configured to couple the third rail member to the first rail member.

8 Claims, 6 Drawing Sheets

(56) References Cited

FOREIGN PATENT DOCUMENTS

| JP | 8-131427 A | 5/1996 |
|----|------------|--------|
| JP | 2003-10164 A | 1/2003 |
| JP | 2004-160263 A | 6/2004 |
| JP | 2011-203668 A | 10/2011 |

OTHER PUBLICATIONS

Written Opinion, issued by International Searching Authority in corresponding International Application No. PCT/KR2014/006824, dated Oct. 28, 2014, (PCT/ISA/237).

* cited by examiner

X-RAY IMAGING SYSTEM

TECHNICAL FIELD

Systems consistent with the exemplary embodiments relate to an x-ray imaging system, and more particularly, to an x-ray imaging system having an improved coupling relation between an x-ray detection apparatus and a table for a patient.

BACKGROUND ART

In general, an x-ray imaging system which is used for medical purposes is an apparatus which is configured to obtain an image of, for example, an inside of a human body, by using x-rays. The x-ray imaging system is capable of obtaining an image of an inside of a human body by a method of detecting x-rays which penetrate the human body after radiating the x-rays at a portion of the body to be imaged, such as a head portion or a chest portion of the human body.

The x-ray imaging system is provided with an x-ray tube configured to radiate x-rays at a portion of an object to be imaged, a high voltage generator configured to generate a high voltage that is needed in generating the x-rays, and apparatuses including a moving apparatus configured to move radiating positions and radiating directions of the x-rays. In addition, the x-ray imaging system is provided with a manipulation apparatus provided such that a user can manipulate and control the apparatuses.

The x-ray imaging system includes an x-ray detection apparatus configured to transmit digital data to a PC after receiving the radiated x-rays and then convert the radiated x-rays into digital signals. The x-ray detection apparatus may be installed at a stand configured to perform x-ray imaging in a state where a patient is in a standing position, or may be installed at a table for a patient, which is configured to perform x-ray imaging in a state where a patient is in a lying position. A case when the x-ray detection apparatus is fixed may be present. However, an x-ray detection apparatus which is manufactured so as to be detachably installed and thus capable of being simultaneously used at a standing position and at the table for imaging a patient is being currently used.

In a case when the x-ray detection apparatus is provided at the table for a patient, the x-ray detection apparatus may be provided so as to be withdrawn in the table.

DISCLOSURE OF INVENTION

Technical Problem

The x-ray detection apparatus can be separated from a table for a patient due to a small force, and damage to a rail unit due to a long period of use.

Solution to Problem

In accordance with aspect of an exemplary embodiment, an x-ray imaging system includes an imaging apparatus configured to generate x-rays and image a subject by radiating the x-rays, an x-ray detection apparatus configured to detect the x-rays by receiving the x-rays radiated by the imaging apparatus, a table on which the subject is positioned, an accommodation frame provided on at least one portion of the table wherein the x-ray detection apparatus is accommodated in the accommodation frame, and a rail unit coupled to an inner side of the accommodation frame configured to at least one of withdraw the x-ray detection apparatus into the accommodation frame and accommodate the x-ray detection apparatus in the accommodation frame, wherein the rail unit comprises a first rail member positioned at an outer side, a second rail member positioned at an inner side of the first rail member, a third rail member positioned in between the first rail member and the second rail member, and a coupling member configured to couple the third rail member to the first rail member.

The coupling member may include a magnetic member, and may be configured to couple the first rail member to the third rail member via a magnetic force.

The coupling member may be coupled to the third rail member.

The coupling member may further include a bracket configured to couple the magnetic member to at least one portion of the third rail member.

The bracket may include a first bracket which is coupled to an upper surface of the third rail member and a second bracket which is coupled to a lower surface of the third rail member.

The coupling member may include a first coupling member configured to couple the magnetic member to the first bracket, a second coupling member configured to couple the first bracket to the third rail member, and a third coupling member configured to couple the first bracket to the second bracket.

The coupling member may include an elastic member to couple the first rail member to the third rail member via an elastic restoring force.

The first rail member may move from the second rail member in a sliding manner, and the third rail member may move from the first rail member in a sliding manner.

The rail unit may be coupled to a lower surface of the accommodation frame.

The rail unit may be located in parallel with the accommodation frame.

Advantageous Effects of Invention

The x-ray detection apparatus can be prevented from being separated from a table for a patient due to a small force, and damage to a rail unit due to a long period of use can be prevented.

BEST MODE FOR CARRYING OUT THE INVENTION

Reference will now be made in detail to the exemplary embodiments, examples of which are illustrated in the accompanying drawings, wherein like reference numerals refer to like elements throughout.

Figure 1:
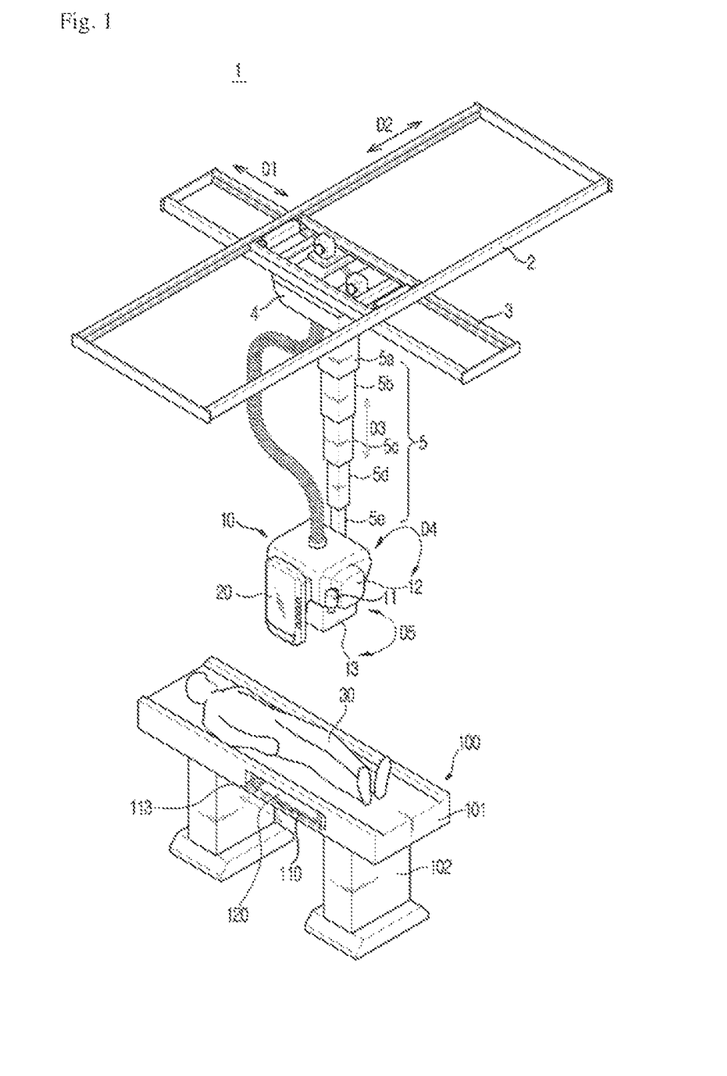
FIG. 1 is a drawing illustrating an x-ray imaging system in accordance with an exemplary embodiment.

FIG. 1 is a drawing illustrating an x-ray imaging system in accordance with an exemplary embodiment.

As illustrated on FIG. 1, an x-ray imaging system 1 includes guide rail 2 and guide rail 3, a moving carriage 4, a post frame 5, an imaging apparatus 10, and a driving apparatus (not shown).

Guide rail 2 and guide rail 3, the moving carriage 4, and the post frame 5 are provided so as to move the imaging apparatus 10 toward a subject 30 to be tested.

The guide rail 2 and guide rail 3 are a first guide rail 2 and a second guide rail 3 installed so as to form a predetermined angle with respect to each other. The first guide rail 2 and the second guide rail 3 may be extended toward a direction which is orthogonal with respect to each other.

The first guide rail 2 is installed at a ceiling of a test room at which the x-ray imaging system 1 is installed. The second guide rail 3 is positioned at a lower side of the first guide rail 3, and is movably mounted at the first guide rail 2 in a sliding manner. A roller capable of moving along the first guide rail 2 may be installed at the first guide rail 2. The second guide rail 3 may be moved along the first guide rail 2 while connected to the roller.

A first direction 'D1' is defined as a direction in which the first guide rail 2 is extended, and a second direction 'D2' is defined as a direction in which the second guide rail 3 is extended. Thus, the first direction 'D1' and the second direction 'D2' may be parallel with respect to the ceiling of the test room while being orthogonal with respect to each other The moving carriage 4 is disposed at a lower side of the second guide rail 3 so as to be moved along the second guide rail 3. A roller movably provided along the second guide rail 3 may be installed at the moving carriage 4.

The post frame 5 is positioned at a lower side of the moving carriage 4 while fixed to the moving carriage 4. The post frame 5 may be provided with a plurality of posts 5a, 5b, 5c, 5d, and 5e. The plurality of posts 5a, 5b, 5c, 5d, and 5e are connected in a foldable manner with respect to each other such that the post frame 5 may be provided so that its length can increase or decrease in a vertical direction of the test room while being fixed to the moving carriage 4. A third direction 'D3' is defined as a direction in which the length of the post frame 5 is increased or decreased. Thus, the third direction 'D3' may be orthogonal with respect to the first direction 'D1' and the second direction 'D2'.

The imaging apparatus 10 is an apparatus configured to radiate x-rays at the subject 30. In general, the imaging apparatus 10 may be an x-ray tube that the x-ray imaging system 1 is provided with. The x-ray tube may be provided with an x-ray generator 11, and a collimator 12 configured to guide x-rays being generated toward the subject 30.

The x-ray generator 11 includes an x-ray tube, and the x-ray tube may be implemented with a two-electrode tube provided with an anode and a cathode. Thermal electrons are generated by having an inside of the x-ray tube in a high vacuum state at about 10 mmHg and then by heating a cathode filament. As for the filament, a tungsten filament may be used, and the filament may be heated by applying a voltage at about 10V and a current at about 3 A to about 5 A at an electrical wire connected to the filament.

Then, x-rays are generated when the thermal electrons collide at a target subject of the anode, as the thermal electrons are accelerated after a high voltage at about 10 kvp to about 300 kvp is engaged in between the anode and the cathode. The generated x-rays are radiated externally through a window, and as for the material of the window, a barium thin film may be used. At this time, most of the energy of the electrons colliding with the target material is consumed as heat, and the energy remaining after being consumed as heat is converted into x-rays.

The anode is mainly structured with copper, as the target material is disposed at a side facing with respect to the cathode, and as for the target material, a high resistance material such as chromium (Cr), iron (Fe), cobalt (Co), nickel (Ni), tungsten (W), and molybdenum (Mo) may be used. The target material may be rotated by a rotating magnetic field. As the target material is rotated, the impact area of the electrons is increased, and when compared to a case of the target material being fixed, the heat accumulation rate may be increased by more than about ten times per unit area.

In addition, other than the above, a high voltage generator (not shown) configured to generate a high voltage needed in generating x-rays may further be included.

A voltage being applied in between the anode and the cathode of the x-ray tube is referred to as a tube voltage, and the tube voltage is applied at the high voltage generator (not shown), and the size thereof may be displayed in kilovolt peak (kvp). As the tube voltage is increased, the velocity of the thermal electrons is increased, and consequently, the energy of the x-rays (the energy of photons) being generated is increased as the thermal electrons collide at the target material. The current that flows at the x-ray tube is referred to as a tube current, and the tube current may be displayed in milli ampere (mA). As the tube current is increased, the number of the thermal electrons being released from the filament is increased, and consequently, the amount of rays of the x-rays (the number a photons of the x-rays) being generated is increased as the thermal electrons are collided at the target material.

Thus, the energy of the x-rays may be controlled by the tube voltage, and the strength or the amount of rays of the x-rays may be controlled by the exposure time of the tube current and the x-rays.

A rotating joint 13 is disposed in between the imaging apparatus 10 and the post frame 5. The rotating joint 13 is configured to couple the imaging apparatus 10 to the post frame 5, and is configured to support the weight applied at the imaging apparatus 10. The rotating joint 13 may be rotatable at a plane surface provided to be perpendicular with respect to the third direction 'D3', and this direction is defined as a fourth direction 'D4'. In addition, the rotating joint 13 may be rotatable in a rotating direction of an axis that is parallel with respect to the first direction 'D1' or the second direction 'D2', and this direction is defined as a fifth direction 'D5'.

The imaging apparatus 10 may be able to be rotatably moved toward the fourth direction 'D4' and the fifth direction 'D5' while connected to the rotating joint 13. In addition, the imaging apparatus 10 may be linearly moved toward the first direction 'D1', the second direction 'D2' and the third direction 'D3' while connected to the post frame 5 by the rotating joint 13.

The driving apparatus (not shown) is provided so as to move the imaging apparatus 10 toward the first direction 'D1', the second direction 'D2', the third direction 'D3', the fourth direction 'D4', and the fifth direction 'D5'. The driving apparatus (not shown) may be a motor which is electrically driven. Each driving apparatus may be connected to a driving force delivering means (not shown) such that the imaging apparatus 10 may be linearly or rotatively moved toward the first direction 'D1', the second direction 'D2', the third direction 'D3', the fourth direction 'D4', and the fifth direction 'D5'. The driving force delivering means (not shown) may be one of a belt and pulley, a chain and sprocket, and a shaft that are generally being used.

The x-ray imaging system 1 may be provided with an x-ray detection apparatus 120. In accordance with an exemplary embodiment, the x-ray detection apparatus 120 is accommodated in a table for a patient 100. Although a human patient is shown in FIG. 1, this is merely an example. Any animal or object which is to be imaged can be used.

The x-ray detection apparatus 120 is configured to receive x-rays that are generated at the imaging apparatus 10 and have penetrated the subject 30, and is capable of diagnosing results in real time after converting the received x-rays into electrical signals that are proportional with respect to the strength of the received x-rays. As an exemplary embodiment, the x-ray detection apparatus 120 may include a light receiving element at which an electrical charge is generated when the photons of the x-rays have arrived, and a reading circuit configured to read and process the electrical signals from the electrical charge. With respect to the material being used as the light receiving element, amorphous silicon (a-Si), amorphous selenium (a-Se), Cadmium zinc telluride (CdZnTe), Mercury (II) iodide (HgI2), or Lead (II) iodide (PbI2) may be included.

Meanwhile, the x-ray detection apparatus 120, depending on a method of obtaining the electrical signals, may be divided into a charge integration mode configured to obtain signals from electrical charge after storing the electrical charge for a predetermined period of time, and a photon counting mode configured to count the number of photons each time when a signal is generated from a single x-ray photon. The x-ray detection apparatus 120 in accordance with an exemplary embodiment may be applied with any one method of the charge integration mode and the photon counting mode.

In accordance with an exemplary embodiment, x-ray imaging may be performed in a state when the subject 30 is positioned on the table for a patient 100. The table for a patient 100 may include a top board 101 at which the subject 30 is positioned, and a supporting unit 102 configured to support the top board 101.

An accommodation frame 110 into which the x-ray detection apparatus 120 may be inserted may be provided at a lower portion of the top board 101. The x-ray detection apparatus 120 may be moved toward a vertical direction according to the driving of a lever 113 while inserted into the accommodation frame 110. In addition, at least one portion of the x-ray detection apparatus 120 may be rotated by driving a rotating unit (not shown) at a lower portion of the accommodation frame 110.

A manipulation unit 20, which is configured to provide an interface capable of inputting information with respect to x-ray imaging and for manipulating each apparatus, is provided at a side surface of the imaging apparatus 10.

Figure 2:
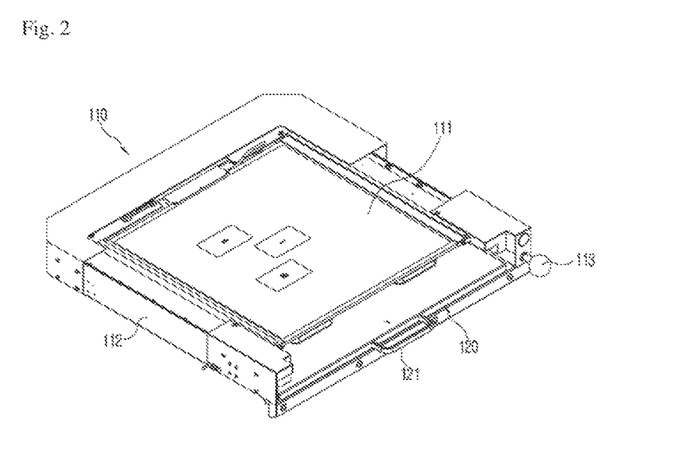
FIG. 2 is a drawing illustrating an accommodation frame at which an x-ray detection apparatus of the x-ray imaging system is accommodated in accordance with an exemplary embodiment.
Figure 3:
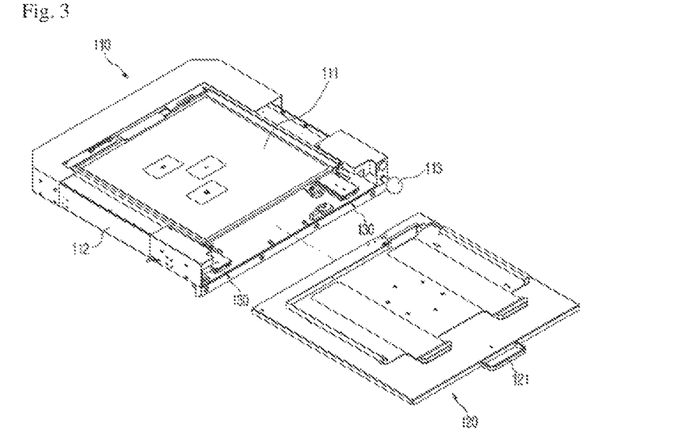
FIG. 3 is a drawing illustrating a state of the x-ray detection apparatus being withdrawn from the accommodation frame of the x-ray imaging system in accordance with an exemplary embodiment.
Figure 4:
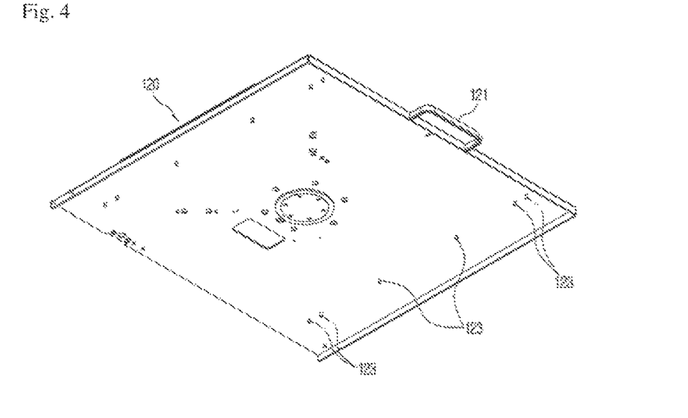
FIG. 4 is a drawing illustrating a lower surface of the x-ray detection apparatus of the x-ray imaging system in accordance with art exemplary embodiment.

FIG. 2 is a drawing illustrating the accommodation frame at which an x-ray detection apparatus of the x-ray imaging system is accommodated in accordance with an exemplary embodiment, FIG. 3 is a drawing, illustrating a state of the x-ray detection apparatus being withdrawn from the accommodation frame of the x-ray imaging system in accordance with an exemplary embodiment, and FIG. 4 is a drawing illustrating a lower surface of the x-ray detection apparatus of the x-ray imaging system in accordance with an exemplary embodiment.

As illustrated in FIG. 2 to FIG. 4, the x-ray detection apparatus 120 may be positioned so as to be inserted toward an inner side of the accommodation frame 110 and therefore, the x-ray detection apparatus 120 can be taken out or inserted into the accommodation frame 110. A cover 111 may be coupled into a base 112 of the accommodation frame 110. The lever 113, which is configured to adjust horizontal movements of the x-ray detection apparatus 120, may be positioned at one side of the accommodation frame 110.

A handle 121 is configured to guide a withdrawing of the x-ray detection apparatus 120 into the accommodation frame 110 and may be positioned at a front of the x-ray detection apparatus 120. A user may be able to insert the x-ray detection apparatus 120 into the accommodation frame 110 while gripping the handle 121, or may be able to withdraw the x-ray detection apparatus 120 from the accommodation frame 110.

A rail unit 130 which is used so as to insert or withdraw the x-ray detection apparatus 120 may be provided at an inside the accommodation frame 110. The rail unit 130 may be coupled into a lower surface of the accommodation frame 110. The rail unit 130 may be disposed in a parallel manner at an inside of the accommodation frame 110. That is, the rail unit 130 in accordance with an exemplary embodiment is coupled into the lower surface instead of a side wall of the accommodation frame 110, and accordingly, the side wall of the accommodation frame 110 does not need to be provided with a certain height, and therefore, the thickness of the accommodation frame 110 may be provided in a thin manner. Accordingly, the thickness of the x-ray detection apparatus 120 may also be manufactured so as to be thin. However, as the rail unit 130 is coupled into the lower surface having a large area, an operational force may be increased while inserting or withdrawing the x-ray detection apparatus 120. However, in accordance with an exemplary embodiment, the degree of withdrawing or inserting of the x-ray detection apparatus 120 may be adjusted according to the force being applied by a user. The above will be described later.

A protrusion unit 123, which is protrudedly provided toward a lower direction, is provided at a lower surface of the x-ray detection apparatus 120, and may be coupled into a groove of the rail unit 130, which is to be described later. Accordingly, the x-ray detection apparatus 120 can be moved along with at least one portion of the rail unit 130.

Figure 5:
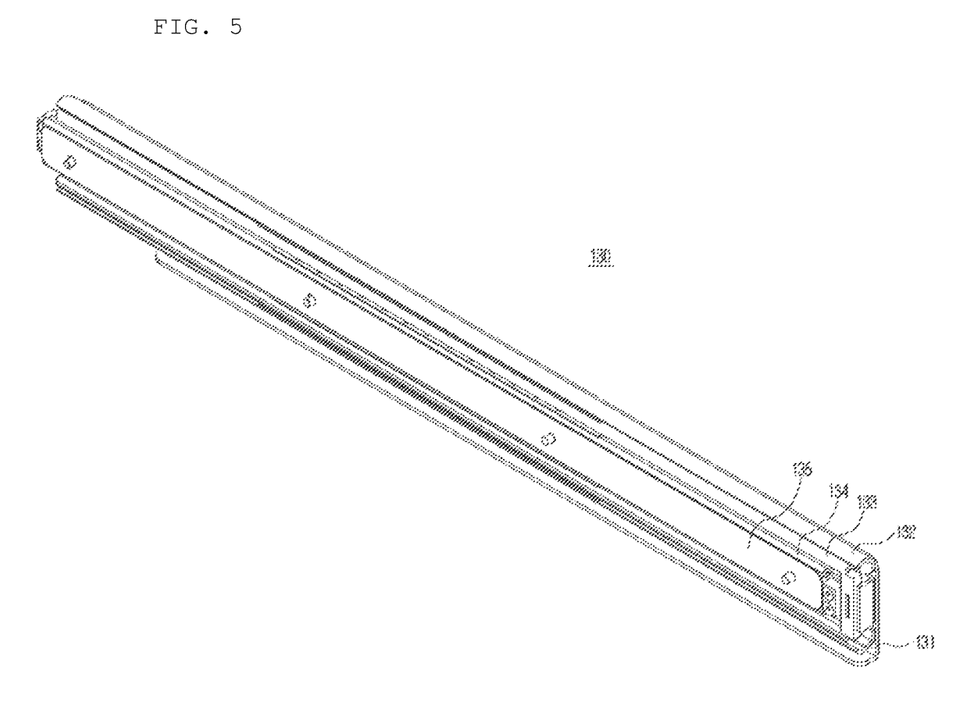
FIG. 5 is a drawing illustrating a rail unit of the accommodation frame of the x-ray imaging system in accordance with an exemplary embodiment.
Figure 6:
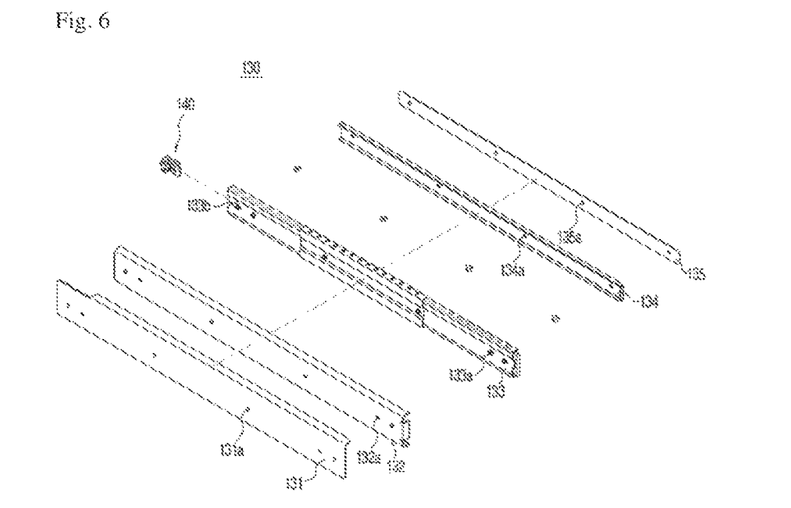
FIG. 6 is an exploded view illustrating the rail unit of FIG. 5.

FIG. 5 is a drawing illustrating the rail unit of the accommodation frame of the x-ray imaging system in accordance with an exemplary embodiment, and FIG. 6 is an exploded view illustrating the rail unit of FIG. 5.

As illustrated in FIG. 5 and FIG. 6, the rail unit 130 may include a first rail member 132 positioned at an outer side, a second rail member 134 positioned at an inner side of the first rail member 132, and a third rail member 133 positioned in between the first rail member 132 and the second rail member 134. That is, the third rail member 133 is inserted into the first rail member 132, and the second rail member 134 is inserted into the third rail member 133.

In addition, a coupling member 140 configured to couple the third rail member 133 to the second rail member 134 is included. The coupling member 140 is provided so as to prevent the third rail member 133 from being easily separated from the first rail member 132. In accordance with an exemplary embodiment, the coupling member 140 may be coupled to an upper surface of the third rail member 133. A coupling groove 133*b* configured such that the coupling member 140 is coupled to the coupling groove 133*b* may be provided at an upper surface of the third rail member 133. Accordingly, the coupling member 140 may be positioned in between the first rail member 132 and the third rail member 133. With respect to the coupling member 140, descriptions will be provided later.

A first cover member 131 to which the x-ray detection apparatus 120 is coupled and configured to reinforce a strength of the rail unit 130 may be coupled to an upper surface of the first rail member 132. In addition, a second cover member 135 coupled into the accommodation frame 110 and configured to reinforce the strength of the rail unit 130 may be coupled to a lower surface of the second rail member 134. The first cover member 131 is provided to surround at least one portion of the first rail member 132, and the second cover member 135 may be able to surround at least one portion of the second rail member 134.

Grooves 131*a* and 132*a* having shapes corresponding to the protrusion unit 123 may be provided at the first cover member 131 and the first rail member 132 such that the protrusion unit 123 of the x-ray detection apparatus 120 may be coupled into the grooves 131*a* and 132*a*. In addition, a groove 133*a* configured so as to provide a coupling of the x-ray detection apparatus 120 may be provided at the third rail member 133 as well.

Grooves 134*a* and 135*a*, which are configured so as to be coupled into the accommodation frame 110, may be provided at the second cover member 135 and the second rail member 134.

Figure 7:
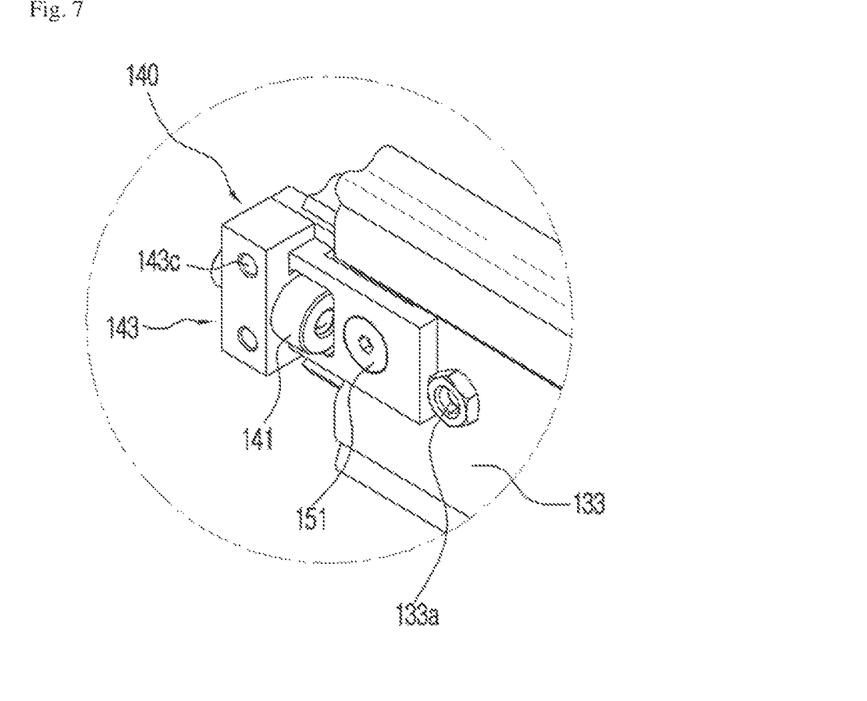
FIG. 7 is an enlarged view of a coupling member of the rail unit of the x-ray imaging system in accordance with an exemplary embodiment.
Figure 8:
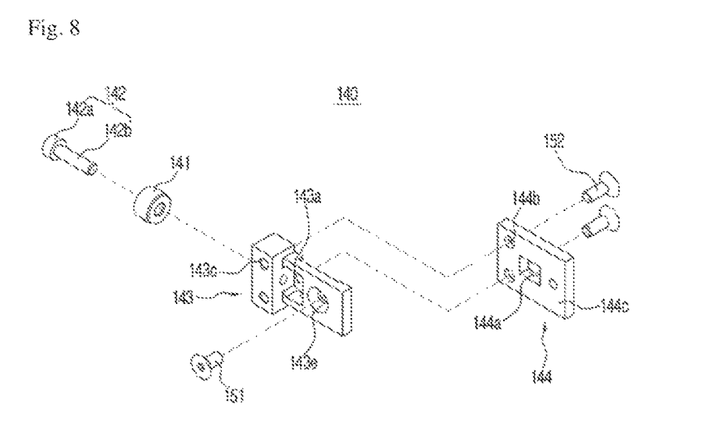
FIG. 8 is an exploded view illustrating the coupling member illustrated on FIG. 7.

FIG. 7 is an enlarged view of the coupling member of the rail unit of the x-ray imaging system in accordance with an exemplary embodiment, and FIG. 8 is an exploded view illustrating the coupling member illustrated on FIG. 7.

As illustrated in FIG. 7 and FIG. 8, the coupling member 140 in accordance with an exemplary embodiment may include a magnetic member 141. According to the above, the first rail member 132 and the third rail member 133 may be coupled into each other by using a magnetic force, and in a case when a force that is larger than the magnetic force is applied, the third rail member 133 may be separated and withdraw from the first rail member 132.

The coupling member 140 in accordance with an exemplary embodiment may further include brackets 143 and 144 configured to accommodate the magnetic member 141. The brackets 143 and 144 may be a first bracket 143 which is coupled into an upper surface of the third rail member 133, and a second bracket 144 which is coupled into a lower surface of the third rail member 133.

A first bracket accommodation unit 143*a* is configured to accommodate the magnetic member 141 and is provided at the first bracket 143, and the first coupling member 142 is configured to fix the magnetic member 141 while the magnetic member 141 is inserted into the first bracket accommodation unit 143*a*. The magnetic member 141 is coupled to the first bracket 143 when the magnetic member 141 is inserted into the first bracket accommodation unit 143*a*. In addition, a second bracket accommodation unit 144*a*, at which the magnetic member 141 which protrudes from the first bracket 143 may be accommodated, may be provided at the second bracket 144.

A first hole 143*e* into which a second coupling member 151 is coupled so as to couple the brackets 143 and 144 into the third rail member 133 may be provided at the first bracket 143. A second coupling member 151 is coupled into the coupling groove 133*b* of the third rail member 133 after penetrating through the first hole 143*e*.

A second hole 143*c* into which a third coupling member 152 is coupled, so as to couple the second bracket 144 and the first bracket 143, may be provided at the first bracket 143, and a third hole 144*b* may be provided at the second bracket 144 at a position corresponding to the second hole 143*c*.

In accordance with an exemplary embodiment, the coupling of the first rail member 132 and the third rail member 133 is mediated by the magnetic member 141, and only when a force that is larger than the magnetic force is applied, the magnetic member 141 can be separated from the third rail member 133 and the first rail member 132. According to the above, an abrupt withdrawing of the x-ray detection apparatus 120 as the third rail member 133 is separated may be prevented, and at the same time, the thin-film type x-ray detection apparatus 120 which has a thin thickness may be used.

In accordance with an exemplary embodiment, the first rail member 132 and the third rail member 133 are coupled into each other by the use of the magnetic member 141, but the exemplary embodiments are not limited hereto. A case of the first rail member and the third rail member being coupled into each other by use of an elastic member may be present. In the case of an elastic member, the first rail member 132 and the third rail member 133 are coupled into each other by using an elastic restoring force, and when a force that is larger than the elastic restoring force is applied, the third rail member 133 may be separated from the first rail member 132.

Figure 9A:
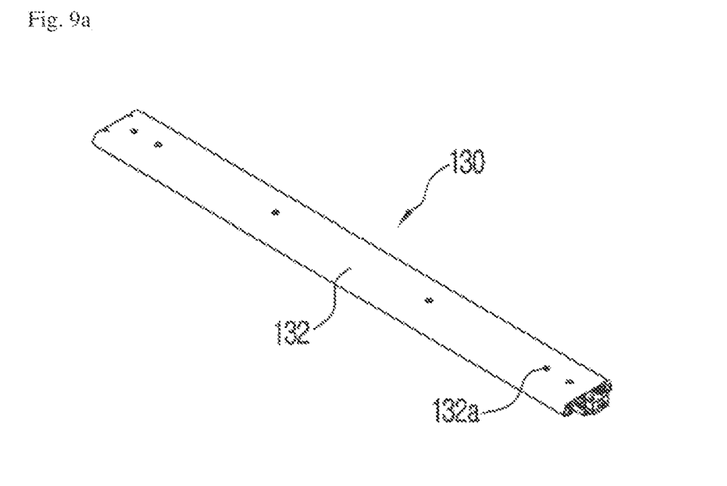
FIGS. 9A, 9B and 9C are drawings illustrating a withdrawing order of each rail member which are the components of the rail unit of the x-ray imaging system in accordance with an exemplary embodiment.
Figure 9B:
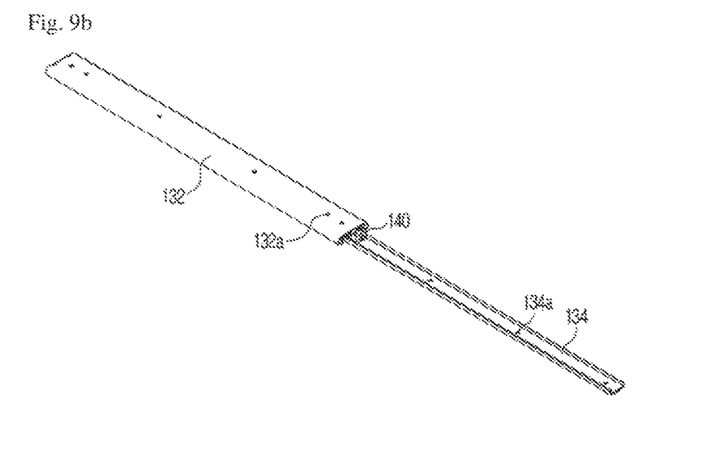
Figure 9C:
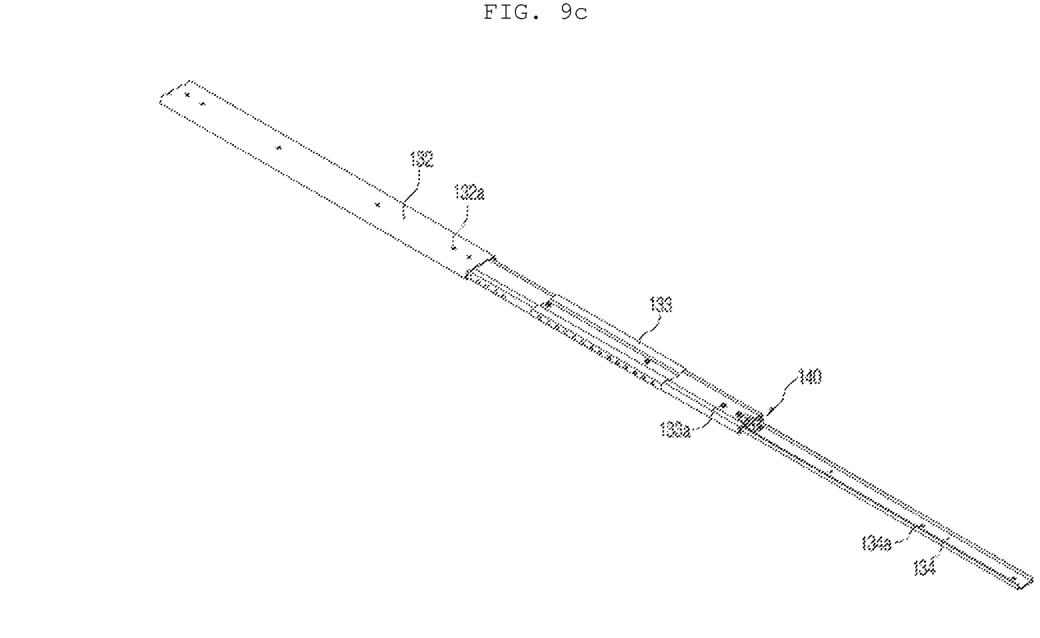

FIGS. 9A, 9B and 9C are drawings illustrating a withdrawing order of each rail member which are components that make up the rail unit of the x-ray imaging system in accordance with an exemplary embodiment.

FIG. 9A is a drawing illustrating the rail unit 130 in a state when the x-ray detection apparatus 120 is not being withdrawn. FIG. 9B is a drawing illustrating a state when the first rail member 132 is being withdrawn from the second rail member 134, and FIG. 9C is a drawing illustrating a state when the third rail member 133 is being withdrawn from the first rail member 132.

Conventionally, the first rail member is withdrawn from the third rail member, and the third rail member is withdrawn from the second rail member, and in the case as the above, a deformation of the third rail member positioned in between the first rail member and the second rail member while provided with weak strength may be occurred. In addition, an inconvenience at the time of withdrawing the x-ray detection apparatus 120 was present as the third rail member is abruptly withdrawn from the second rail member.

However, in accordance with an exemplary embodiment, in a case when a force that is larger than a certain level is not applied, the first rail member 132 and the third rail member 133 are simultaneously moved, and thus an abrupt withdrawal of the x-ray detection apparatus 120 may be prevented. In addition, as the first rail member 132 is provided to wrap around the third rail member 133, a deformation of the third rail member 133 may be prevented.

Although a few exemplary embodiments have been shown and described, it would be appreciated by those skilled in the art that changes may be made in these exemplary embodiments without departing from the principles and spirit of the disclosure, the scope of which is defined in the claims and their equivalents.

The invention claimed is:

1. An x-ray imaging system, comprising:
   an imaging apparatus configured to generate x-rays and image a subject by radiating the x-rays;
   an x-ray detection apparatus configured to detect the x-rays by receiving the x-rays radiated by the imaging apparatus;
   a table on which the subject is positioned;
   an accommodation frame provided on at least one portion of the table, wherein the x-ray detection apparatus is accommodated in the accommodation frame; and
   a rail unit coupled to an inner side of the accommodation frame configured to at least one of withdraw the x-ray detection apparatus from the accommodation frame and accommodate the x-ray detection apparatus in the accommodation frame, wherein the rail unit comprises:
   a first rail member positioned at an outer side;
   a second rail member positioned at an inner side of the first rail member;
   a third rail member positioned in between the first rail member and the second rail member; and
   a coupling member configured to couple the third rail member to the first rail member via a magnetic force such that the third rail member and the first rail member move simultaneously, wherein the coupling member comprises:
   a magnetic member; and
   a bracket provided to accommodate the magnetic member, the bracket including a first bracket which is coupled to a first surface of the third rail member, and the bracket further including a second bracket which is coupled to a second surface of the third rail member.

2. The x-ray imaging system of claim 1, wherein the coupling member is coupled to the third rail member.

3. The x-ray imaging system of claim 1, wherein the coupling member further comprises:
   a first coupling member configured to couple the magnetic member to the first bracket;
   a second coupling member configured to couple the first bracket to the third rail member; and
   a third coupling member configured to couple the first bracket to the second bracket.

4. The x-ray imaging system of claim 1, wherein the first rail member moves from the second rail member in a sliding manner, and the third rail member moves from the first rail member in a sliding manner.

5. The x-ray imaging system of claim 1, wherein the rail unit is coupled to a lower surface of the accommodation frame.

6. The x-ray imaging system of claim 1, wherein the rail unit is located parallel with the accommodation frame.

7. The x-ray imaging system according to claim 1, wherein the first rail member at least partially wraps around the third rail member.

8. An x-ray imaging system, comprising:
   an imaging apparatus configured to transmit X-rays towards an object; and
   an x-ray detection apparatus configured to receive the X-rays transmitted through the object, wherein the x-ray detection apparatus comprises a rail unit comprising:
   a first rail member;
   a second rail member positioned at an inner side of the first rail member;
   a third rail member positioned in between the first rail member and the second rail member; and
   a coupling member configured to couple the third rail member to the first rail member via a magnetic force such that the third rail member and the first rail member move simultaneously, wherein the coupling member comprises:
   a magnetic member; and
   a bracket provided to accommodate the magnetic member, the bracket including a first bracket which is coupled to a first surface of the third rail member, and the bracket further including a second bracket which is coupled to a second surface of the third rail member.

* * * * *